United States Patent
Schmitt et al.

(10) Patent No.: US 7,189,679 B2
(45) Date of Patent: Mar. 13, 2007

(54) HERBICIDAL 3-AMINO-2-THIOMETHYLBENZOYLPYRAZOLES

(75) Inventors: Monika Schmitt, Frankfurt a. M. (DE); Andreas van Almsick, Karben (DE); Lothar Willms, Hofheim (DE); Thomas Auler, Bad Soden (DE); Heinz Kehne, Hofheim (DE); Martin Hills, Idstein (DE); Dieter Feucht, Eschborn (DE)

(73) Assignee: Bayer CropScience GmbH, Frankfurt am Main (DE)

( * ) Notice: Subject to any disclaimer, the term of this patent is extended or adjusted under 35 U.S.C. 154(b) by 153 days.

(21) Appl. No.: 11/097,931

(22) Filed: Apr. 1, 2005

(65) Prior Publication Data

US 2005/0221988 A1    Oct. 6, 2005

(30) Foreign Application Priority Data

Apr. 3, 2004    (DE)    ............. 10 2004 016 496

(51) Int. Cl.
*A01N 43/84* (2006.01)
*A01N 43/60* (2006.01)
*A01N 43/78* (2006.01)
*C07D 413/04* (2006.01)
*C07D 231/10* (2006.01)

(52) U.S. Cl. ............. 504/225; 504/235; 504/263; 504/265; 504/266; 544/140; 544/333; 544/371; 546/211; 548/131; 548/356.1

(58) Field of Classification Search ............. 504/235, 504/263, 265, 266; 544/140, 333, 371; 546/211; 548/131, 356.1

See application file for complete search history.

(56) References Cited

U.S. PATENT DOCUMENTS 5,013,659 A    5/1991    Bedbrook et al.
5,824,802 A    10/1998    Benko et al.

FOREIGN PATENT DOCUMENTS

| EP | 0 186 117 B1 | 11/1990 |
| EP | 0 193 259 B1 | 12/1991 |
| EP | 0 142 924 B1 | 4/1992 |
| EP | 0 240 001 B1 | 7/1992 |
| EP | 0 221 044 B1 | 9/1992 |
| EP | 0 242 246 B1 | 11/1992 |
| EP | 0 242 236 B2 | 8/1996 |
| EP | 0 369 803 B2 | 8/1996 |
| EP | 0 257 993 B1 | 11/1996 |
| WO | WO-91/13972 | 9/1991 |
| WO | WO-91/19806 | 12/1991 |
| WO | WO-92/00377 | 1/1992 |
| WO | WO-92/11376 | 7/1992 |
| WO | WO-92/14827 | 9/1992 |
| WO | WO-96/26202 | 8/1996 |
| ZA | 9601344 A | 8/1996 |

*Primary Examiner*—Kamal A. Saeed
(74) *Attorney, Agent, or Firm*—Connolly Bove Lodge & Hutz LLP

(57) ABSTRACT

3-Amino-2-thiomethylbenzoylpyrazoles of the formula (I) and their use as herbicides are described.

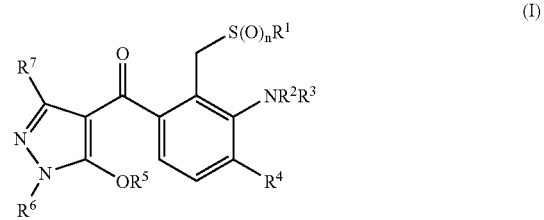

In this formula (I) $R^1$ to $R^9$ are various radicals.

17 Claims, No Drawings

HERBICIDAL 3-AMINO-2-THIOMETHYLBENZOYLPYRAZOLES

The invention pertains to the technical field of herbicides, particularly that of herbicides from the benzoylpyrazole class, for selectively controlling broadleaf and gramineous weeds in crops of useful plants.

From a variety of publications it is already known that certain benzoyl derivatives possess herbicidal properties. For instance, U.S. Pat. No. 5,824,802 discloses benzoylpyrazolones which carry in position 3 of their phenyl ring an amino group and in position 2 various radicals. These compounds, however, frequently exhibit a herbicidal activity which is inadequate, or an adequate tolerance by crop plants.

It is an object of the present invention to provide further herbicidally effective compounds having herbicidal properties which are improved over those of the prior art compounds.

It has now been found that certain 4-benzoylpyrazoles which carry in position 3 of their phenyl ring an amino group and in position 2 a thiomethyl group are especially suitable herbicides. The present invention accordingly first provides compounds of the formula (I) or salts thereof

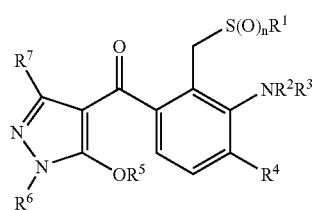

(I)

in which the radicals and indices have the following definitions:

$R^1$ is $C_1$–$C_6$alkyl;

$R^2$ and $R^3$ independently of one another are hydrogen, $C_3$–$C_6$cycloalkyl, $C_2$–$C_6$alkenyl, $C_2$–$C_6$alkynyl or $C_1$–$C_6$alkyl substituted s times by radicals from the group consisting of halogen, $C_1$–$C_4$alkoxy and $C_1$–$C_4$alkylthio, or $NR^2R^3$ forms a 5- or 6-membered heterocyclic radical from the group consisting of 1-pyrrolyl, 1-pyrrolidinyl, 1-piperidinyl, 1-pyrazolyl, 1,2,3-triazol-1-yl, 1,2,4-triazol-1-yl, 1-tetrazolyl, 1-pyrazolidinyl, 1-imidazolyl, 2-isoxazoldinyl, 3-oxazolidinyl, 1,2,3-oxadiazolidin-2-yl, 1,2,3-oxadiazolidin-3-yl, 1,2,4-oxadiazolidin-2-yl, 1,2,3-oxadiazolidin-4-yl, 1,3,4-oxadiazolidin-3-yl, 1,3,4-oxadiazolidin-4-yl, 3-thiazolidinyl, 2,3-thiadiazolidin-2-yl, 1,2,3-thiadiazolidin-3-yl, 1,2,4-thiadiazolidin-2-yl, 1,2,3-thiadiazolidin-4-yl, 1,3,4-thiadiazolidin-3-yl, 1,3,4-thiadiazolidin-4-yl, 1-morpholinyl, 2,3-dihydropyrrol-1-yl, 2,5-dihydropyrrol-1-yl, 2,3-dihydroisoxazol-2-yl, 2,5-dihydroisothiazol-1-yl, 1,2-dihydropyridin-1-yl, 1,4-dihydropyridin-1-yl, 3,4,5,6-tetrahydropyridin-1-yl, 1-piperazinyl and 1-tetrahydropyrimidinyl, the aforementioned heterocyclic radicals being substituted s times by substituents from the group consisting of halogen, cyano, $C_1$–$C_4$alkoxy, trifluoromethyl, trifluoroethyl, fluoro-$C_1$–$C_3$alkyl, fluoro-$C_1$–$C_3$alkoxy, cyano-$C_1$–$C_4$alkyl, $C_3$–$C_6$cycloalkyl, $C_3$–$C_6$cycloalkyl-$C_1$–$C_4$-alkyl, $C_1$–$C_3$alkoxymethyl;

$R^4$ is hydrogen, halogen, $C_1$–$C_4$alkyl, halo-$C_1$–$C_4$alkyl, $C_1$–$C_4$alkoxy, $C_1$–$C_4$alkylthio, $C_1$–$C_4$alkylsulfinyl or $C_1$–$C_4$alkylsulfonyl;

$R^5$ is hydrogen, $C_1$–$C_6$alkylcarbonylmethyl, phenylsulfonyl, $C_1$–$C_4$ alkylsulfonyl substituted s times by halogen, phenylsulfonyl substituted once by methyl or halogen, benzyl substituted s times by halogen, nitro or methoxy, or benzoylmethyl substituted s times by halogen, nitro, methyl or methoxy;

$R^6$ is $C_1$–$C_4$alkyl;

$R^7$ is hydrogen, ($C_1$–$C_4$)alkyl or $C_3$–$C_6$cycloalkyl;

n is 0, 1 or 2;

s is 0, 1, 2 or 3;

t is 1, 2 or 3.

Where $R^5$ is hydrogen the compounds of the formula (I) according to the invention, depending on external conditions, such as solvent and pH, may occur in different tautomeric structures:

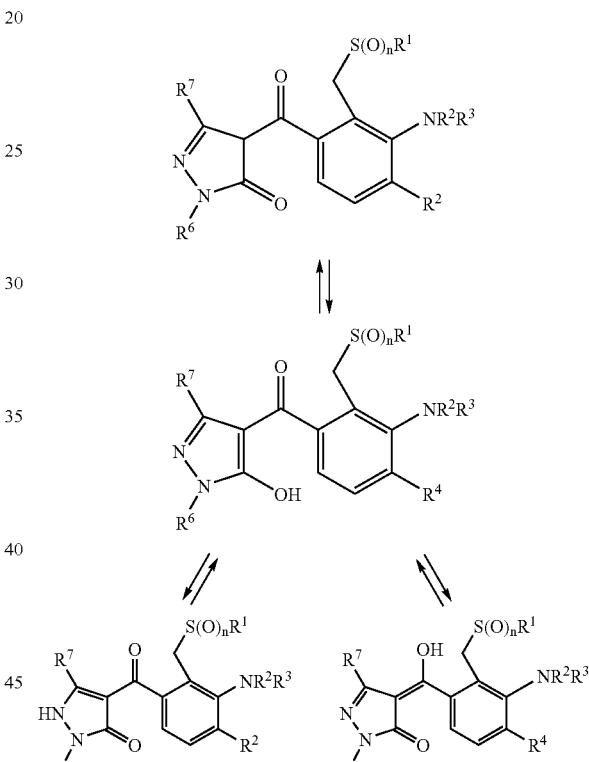

Depending on the nature of the substituents the compounds of the formula (I) contain an acidic proton, which can be removed by reaction with a base. Examples of suitable bases include hydrides, hydroxides, and carbonates of alkali metals and alkaline earth metals, such as lithium, sodium, potassium, magnesium, and calcium, and also ammonia and organic amines such as triethylamine and pyridine. Such salts are likewise provided by the invention.

In formula (I) and all subsequent formulae alkyl radicals having more than two carbon atoms can be straight-chain or branched. Alkyl radicals are for example, methyl, ethyl, n- or i-propyl, n-, i-, t- or 2-butyl, pentyls, hexyls, such as n-hexyl, i-hexyl, and 1,3-dimethylbutyl, preferably methyl or ethyl.

Where a group is multiply substituted by radicals, this means that said group is substituted by one or more, identical or different, radicals selected from those specified.

Cycloalkyl is cyclopropyl, cyclobutyl, cyclopentyl or cyclohexyl.

Halogen is fluorine, chlorine, bromine or iodine. The radicals alkyl, alkoxy, haloalkyl, haloalkoxy and alkylthio, and also the corresponding unsaturated and/or substituted radicals, can in each case be straight-chain or branched in the carbon backbone. Haloalkyl, haloalkenyl and haloalkynyl are alkyl, alkenyl and alkynyl, respectively, that are fully or partly substituted by halogen, preferably by fluorine, chlorine and/or bromine, in particular by fluorine or chlorine, examples being $CF_3$, $CHF_2$, $CH_2F$, $CF_3CF_2$, $CH_2FCHCl$, $CCl_3$, $CHCl_2$, $CH_2CH_2Cl$, $CH=CHCl$, $CH=CCl_2$, $C\equiv CCH_2Cl$; haloalkoxy is, for example $OCF_3$, $OCHF_2$, $OCH_2F$, $CF_3CF_2O$, $OCH_2CF_3$ and $OCH_2CH_2Cl$; corresponding to haloalkenyl and other halogen-substituted radicals.

Where a group is multiply substituted, this means that, with respect to the combination of the various substituents, the general principles of the structure of chemical compounds are observed; in other words, it does not mean that compounds are formed of which the skilled worker is aware that they are chemically unstable or not possible.

Depending on the nature and linking of their substituents the compounds of the formula (I) can exist as stereoisomers. Where, for example, there are one or more asymmetric carbon atoms, enantiomers and diastereomers may occur. Stereoisomers can be obtained from the as-prepared mixtures by standard separation methods, e.g., by chromatographic separation techniques. Likewise, stereoisomers may be prepared selectively using stereoselective reactions and optically active starting materials and/or auxiliaries. The invention also relates to all of the stereoisomers and mixtures thereof which, while embraced by the formula (I), have not been specifically defined.

Compounds of the formula (I) that are of closer interest are those in which $R^1$ is methyl;

$R^2$ and $R^3$ independently of one another are hydrogen, cyclopropyl, $C_1$–$C_6$alkyl, $C_2$–$C_6$alkenyl, $C_2$–$C_6$alkynyl or $C_1$–$C_6$alkyl substituted by a $C_1$–$C_4$alkoxy radical, or $NR^2R^3$ forms a 5- or 6-membered heterocyclic radical from the group consisting of 1-pyrrolyl, 1-pyrrolidinyl, 1-piperidinyl, 1-pyrazolyl, 1,2,3-triazol-1-yl, 1,2,4-triazol-1-yl, 1-tetrazolyl, 1-pyrazolidinyl, 1-imidazolyl, 2-isoxazoldinyl, 3-oxazolidinyl, 1,2,3-oxadiazolidin-2-yl, 1,2,3-oxadiazolidin-3-yl, 1,2,4-oxadiazolidin-2-yl, 1,2,3-oxadiazolidin-4-yl, 1,3,4-oxadiazolidin-3-yl, 1,3,4-oxadiazolidin-4-yl, 3-thiazolidinyl, 2,3-thiadiazolidin-2-yl, 1,2,3-thiadiazolidin-3-yl, 1,2,4-thiadiazolidin-2-yl, 1,2,3-thiadiazolidin-4-yl, 1,3,4-thiadiazolidin-3-yl, 1,3,4-thiadiazolidin-4-yl, 1-morpholinyl, 2,3-dihydropyrrol-1-yl, 2,5-dihydropyrrol-1-yl, 2,3-dihydroisoxazol-2-yl, 2,5-dihydroisothiazol-1-yl, 1,2-dihydropyridin-1-yl, 1,4-dihydropyridin-1-yl, 3,4,5,6-tetrahydropyridin-1-yl, 1-piperazinyl and 1-tetrahydropyrimidinyl, the above-mentioned heterocyclic radicals being substituted s times by substituents from the group consisting of halogen, methoxy and trifluoromethyl;

n is 0 or 2, and the other substituents and indices each have the definitions specified earlier on above.

Preference is given to compounds of the formula (I) in which $R^4$ is bromine, chlorine, fluorine, trifluoromethyl, methylsulfonyl or ethylsulfonyl, and $R^5$ is hydrogen, n-propylsulfonyl or benzoylmethyl, and the other substituents and indices each have the definitions specified earlier on above.

Particular preference is given to compounds of the formula (I) in which $R^6$ is methyl or ethyl;

$R^7$ is hydrogen, methyl or cyclopropyl, and the other substituents and indices each have the definitions specified earlier on above.

Very particular preference is given to compounds of the formula (I) in which $R^2$ and $R^3$ independently of one another are hydrogen, methyl, ethyl, cyclopropyl or methoxyethyl, or $NR^2R^3$ forms a radical from the group consisting of 1-pyrrolyl, 1-pyrazolyl, 1-morpholinyl and 1-piperazinyl, and the other substituents and indices each have the definitions specified earlier on above.

In all formulae below, the substituents and symbols, unless defined otherwise, have the same definition as described under formula (I).

Compounds according to the invention in which $R^5$ is hydrogen and n=0 can be prepared, for example, in accordance with the process indicated in scheme 1 and known from DOS 25 13 750, by base-catalyzed reaction of a benzoyl halide with a pyrazolone, or in accordance with the process indicated in scheme 2 and known, for example, from EP-A 0 186 117, by base-catalyzed reaction of a benzoyl halide with a pyrazolone and subsequent rearrangement.

Scheme 1

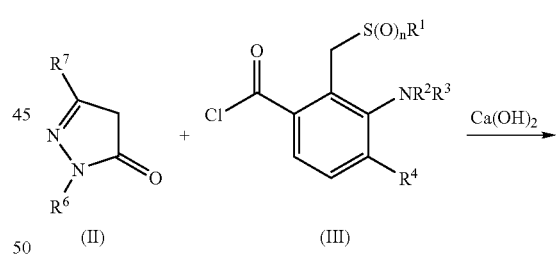

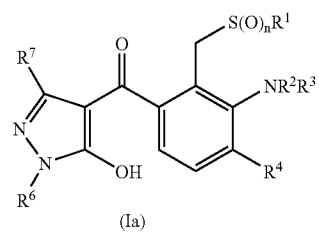

Scheme 2

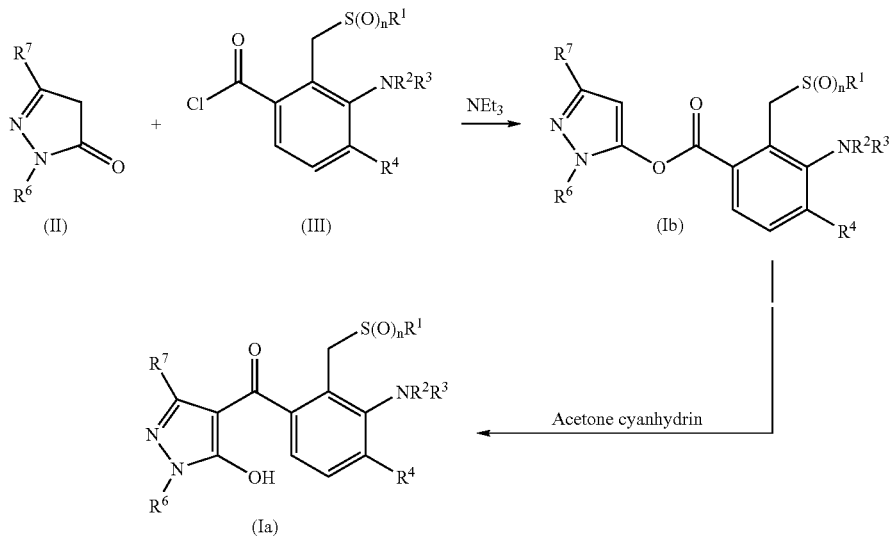

Alternatively the reaction of a pyrazolone (II) may also take place directly with a benzoic acid (IIIa) in the presence of a suitable water-removing agent, such as DCC or EDAC (Ib) (scheme 2a). These methods are described, for example, in EP-A 0369 803.

Scheme 2a

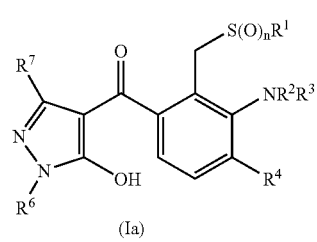

Scheme 2b

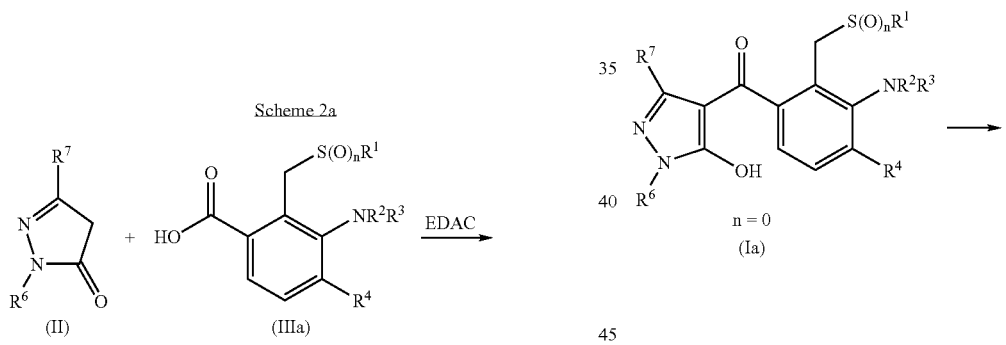

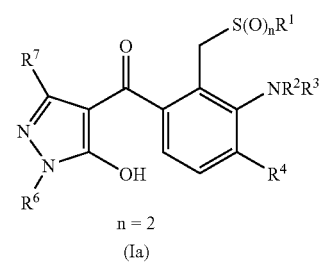

The compounds (Ib) of the invention where n=0 can then be converted by suitable oxidizing agents such as m-chloroperbenzoic acid by methods known from the literature into the compounds (Ib) of the invention where n=1 or 2 (scheme 2b).

Benzoyl chlorides (III) are obtainable from the benzoic acids (IIIa) by methods known from the literature, such as by treatment with oxalyl chloride.

The benzoic acids (IIIa) can be prepared, for example, by the process indicated in scheme 2c and known from U.S. Pat. No. 5,824,802, from the 3-fluorobenzoic acids (IIIb), by reaction with the corresponding amines $HNR^2R^3$.

Scheme 2c

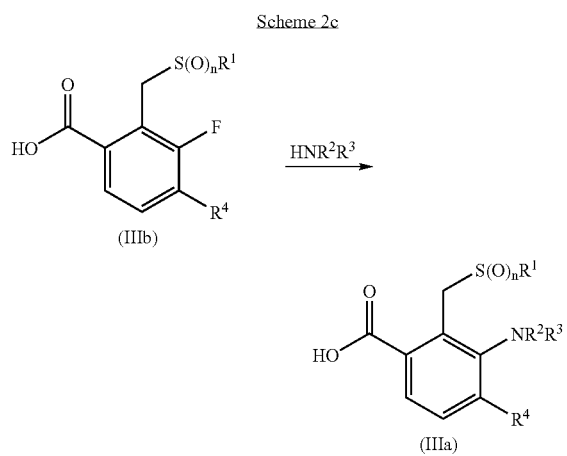

(IIIb)

(IIIa)

The 3-fluorobenzoic acids (IIIb) may be obtained, for example, by the process indicated in scheme 2d, and known in general from the literature, by reaction of the analogous 2-bromomethylbenzoic acids (IIIc) with $NaS(O)_nR^1$ (n=0).

Scheme 2d

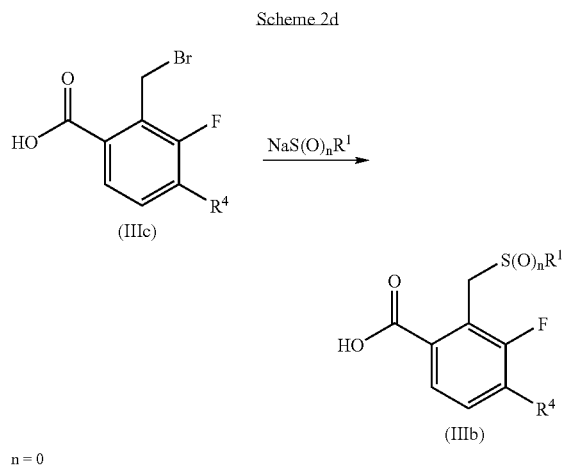

(IIIc)

(IIIb)

n = 0

The 2-bromomethylbenzoic acids (IIIc) can be obtained, for example, by the process indicated in scheme 2e and known in general from the literature, by reaction of the analogous 2-methylbenzoic acids (IIId) with brominating reagents such as bromine or N-bromosuccinimide in the presence of light or free-radical initiators such as dibenzoyl peroxide.

Scheme 2e

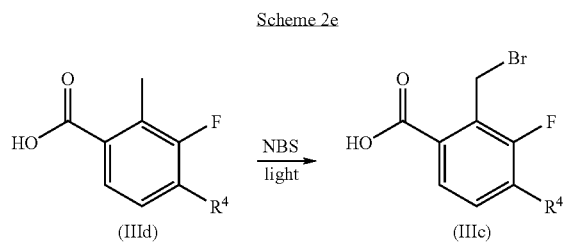

(IIId)

(IIIc)

2-Methylbenzoic acids (IIId) are known from the literature or can be prepared by methods known from the literature.

Compounds of the invention in which $R^5$ has a definition other than hydrogen are prepared in accordance with scheme 3 advantageously from the compounds obtainable according to scheme 1 or 2, by base-catalyzed reaction with a suitable acylating agent $R^5$—X, in which X is a leaving group such as halogen. Methods of this kind are known, for example, from DOS 25 13 750.

Scheme 3

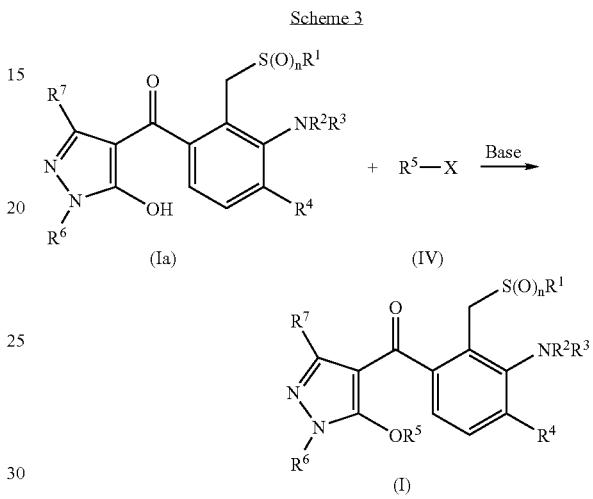

(Ia)

(IV)

(I)

The starting compounds used in the above schemes are either commercial compounds or can be prepared by methods known per se. Thus, the pyrazolones of the formula (II) can be prepared, for example, by the methods described in EP-A 0 240 001 and J. Prakt. Chem. 315, 382, (1973).

The compounds of the formula (I) according to the invention have an excellent herbicidal activity against a broad range of economically important monocotyledonous and dicotyledonous weed plants. The active substances control perennial weeds equally well which produce shoots from rhizomes, root stocks or other perennial organs and which cannot be easily controlled. In this context, it generally does not matter whether the substances are applied before sowing, pre-emergence or post-emergence. Some representatives of the monocotyledonous and dicotyledonous weed flora which can be controlled by the compounds according to the invention may be mentioned individually as examples, but this is not to be taken to mean a restriction to certain species. The monocotyledonous weed species which are controlled well are, for example, *Avena, Lolium, Alopecurus, Phalaris, Echinochloa, Digitaria, Setaria* and *Cyperus* species from the annual group, and *Agropyron, Cynodon, Imperata* and *Sorghum* or else perennial *Cyperus* species amongst the perennial species. In the case of dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from the annual group, and *Convolvulus, Cirsium, Rumex* and *Artemisia* among the perennial weeds. Harmful plants which are found under the specific culture conditions of rice, such as, for example, *Echinochloa, Sagittaria, Alisma, Eleocharis, Scirpus* and *Cyperus* are also controlled outstandingly well by the active substances according to the invention. If the compounds according to the invention are applied to the soil surface prior to germination, then either emergence of the weed seedlings is prevented completely, or the weeds grow until they have reached the cotyledon stage but growth then comes to a standstill and, after a period of three to four weeks, the plants eventually die completely. When the active substances are applied post-emergence to the green parts of the plants, growth also stops drastically very soon after the treatment, and the weeds remain at the growth stage of the time of application, or, after a certain period of time, they die completely so that in this way competition by the weeds, which is detrimental for the crop plants, is thus eliminated at a very early stage and in a sustained manner. In particular, the compounds according to the invention have an outstanding action against *Amaranthus retroflexus, Avena* sp., *Echinochloa* sp., *Cyperus serotinus, Lolium multiflorum, Setaria viridis, Sagittaria pygmaea, Scirpus juncoides, Sinapis* sp. and *Stellaria* media.

The compounds according to the invention have an outstanding herbicidal activity against monocotyledonous and dicotyledonous weeds, and yet crop plants of economically important crops such as, for example, wheat, barley, rye, rice, maize, sugar beet, cotton and soya suffer only negligible damage, if any. In particular, they are outstandingly well tolerated in wheat, maize and rice. This is why the present compounds are highly suitable for the selective control of unwanted vegetation in stands of agricultural useful plants or of ornamentals.

Owing to their herbicidal properties, the active substances can also be employed for controlling weed plants in crops of known plants or genetically modified plants which are yet to be developed. As a rule, the transgenic plants are distinguished by particularly advantageous properties, for example by resistances to certain pesticides, especially certain herbicides, by resistances to plant diseases or causative organisms of plant diseases, such as certain insects or microorganisms such as fungi, bacteria or viruses. Other particular properties concern for example the harvested material with regard to quantity, quality, shelf life, composition and specific constituents. Thus, transgenic plants are known which have an increased starch content or whose starch quality has been modified, or those whose fatty acid composition in the harvested material is different.

The compounds of the formula (I) according to the invention or their salts are preferably employed in economically important transgenic crops of useful plants and ornamentals, for example cereals such as wheat, barley, rye, oats, millet, rice, cassava and maize, or else crops of sugar beet, cotton, soya, oilseed rape, potato, tomato, pea and other vegetables. The compounds of the formula (I) can preferably be employed as herbicides in crops of useful plants which are resistant, or have been genetically modified to be resistant, to the phytotoxic effects of the herbicides.

Conventional routes for the generation of novel plants which have modified properties compared with existing plants are, for example, traditional breeding methods and the generation of mutants. Alternatively, novel plants with modified properties can be generated with the aid of recombinant methods (see, for example, EP-A-0221044, EP-A-0131624). For example, several cases of the following have been described:

recombinant modifications of crop plants for the purposes of modifying the starch synthesized in the plants (e.g. WO 92/11376, WO 92/14827, WO 91/19806), transgenic crop plants which exhibit resistances to certain herbicides of the glufosinate type (cf. eg. EP-A-0242236, EP-A-242246), glyphosate type (WO 92/00377) or of the sulfonylurea type (EP-A-0257993, U.S. Pat. No. 5,013,659)

transgenic crop plants, for example cotton, with the ability to produce *Bacillus thuringiensis* toxins (Bt toxins), which make the plants resistant to certain pests (EP-A-0142924, EP-A-0193259), transgenic crop plants with a modified fatty acid composition (WO 91/13972), A large number of techniques in molecular biology, with the aid of which novel transgenic plants with modified properties can be generated, are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996 or Christou, "Trends in Plant Science" 1 (1996) 423–431.

To carry out such recombinant manipulations, nucleic acid molecules can be introduced into plasmids which permit a mutagenesis or a sequence alteration by recombination of DNA sequences. With the aid of the abovementioned standard processes, it is possible, for example, to carry out base substitutions, to remove part sequences or to add natural or synthetic sequences. The fragments can be provided with adapters or linkers to link the DNA fragments to each other.

Plant cells with a reduced activity of a gene product can be obtained, for example, by expressing at least one corresponding antisense RNA, a sense RNA for achieving a cosuppression effect, or the expression of at least one suitably constructed ribozyme which specifically cleaves transcripts of the abovementioned gene product.

To this end, it is possible, on the one hand, to use DNA molecules which encompass all of the coding sequence of a gene product including any flanking sequences which may be present, but also DNA molecules which only encompass portions of the coding sequence, it being necessary for these portions to be so long as to cause an antisense effect in the cells. Another possibility is the use of DNA sequences which have a high degree of homology with the coding sequences of a gene product, but are not completely identical.

When expressing nucleic acid molecules in plants, the protein synthesized may be localized in any desired compartment of the plant cell. However, to achieve localization in a particular compartment, the coding region can, for example, be linked to DNA sequences which ensure localization in a particular compartment. Such sequences are known to the skilled worker (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated by known techniques to give intact plants. In principle, the transgenic plants can be plants of any desired plant species, i.e. both monocotyledonous and dicotyledonous plants.

Thus, transgenic plants can be obtained which exhibit modified properties owing to the overexpression, suppression or inhibition of homologous (i.e. natural) genes or gene sequences or expression of heterologous (i.e. foreign) genes or gene sequences.

When using the active substances according to the invention in transgenic crops, effects are frequently observed—in addition to the effects against weed plants to be observed in other crops—which are specific for the application in the transgenic crop in question, for example a modified or specifically widened controllable weed spectrum, modified application rates which may be employed for the application, preferably good combining ability with the herbicides to which the transgenic crop is resistant, and an effect on the growth and yield of the transgenic crop plants. The invention therefore also relates to the use of the compounds according to the invention as herbicides for controlling harmful plants in transgenic crop plants.

The substances according to the invention additionally have outstanding growth-regulatory properties in crop plants. They engage in the plants' metabolism in a regulatory fashion and can thus be employed for the targeted influencing of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops, allowing lodging to be reduced or prevented completely.

The compounds according to the invention can be employed in the form of wettable powders, emulsifiable concentrates, sprayable solutions, dusts or granules in the customary preparations. The invention therefore further relates to herbicidal compositions comprising compounds of the formula (I). The compounds of the formula (I) can be formulated in various ways, depending on the prevailing biological and/or chemico-physical parameters. Examples of suitable formulations which are possible are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Technology], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflätchenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Wettable powders are preparations which are uniformly dispersible in water and which, in addition to the active substance, also contain ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutylnaphthalenesulfonate or else sodium oleoylmethyltaurate, in addition to a diluent or inert substance. To prepare the wettable powders, the herbicidal active substances are ground finely, for example in customary equipment such as hammer mills, blowing mills and air-jet mills, and simultaneously or subsequently mixed with the formulation auxiliaries.

Emulsifiable concentrates are prepared by dissolving the active substance in an organic solvent, such as butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which can be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays such as kaolin, bentonite and pyrophyllite, or diatomaceous earth.

Suspension concentrates can be water based or oil based. They can be prepared for example by wet-grinding by means of customary bead mills, if appropriate with addition of surfactants, as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active substance onto adsorptive, granulated inert material or by applying active substance concentrates to the surface of carriers such as sand, kaolinites or granulated inert material with the aid of tackifiers, for example polyvinyl alcohol, sodium polyacrylate or else mineral oils. Suitable active substances can also be granulated in the fashion which is conventional for the production of fertilizer granules, if desired as a mixture with fertilizers.

Water-dispersible granules are generally prepared by customary methods such as spray drying, fluidized-bed granulation, disk granulation, mixing with high-speed stirrers and extrusion without solid inert material.

To prepare disk granules, fluidized-bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8–57.

For further details on the formulation of crop protection products see, for example G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise 1 to 30% by weight of active substance, preferably in most cases 5 to 20% by weight of active substance, and sprayable solutions comprise approximately 0.05 to 80, preferably 2 to 50% by weight of active substance. In the case of water-dispersible granules, the active substance content depends partly on whether the active compound is in liquid or solid form and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the stickers, wetters, dispersants, emulsifiers, penetrants, preservatives, antifreeze agents, solvents, fillers, carriers, colorants, antifoams, evaporation inhibitors, and pH and viscosity regulators which are conventional in each case.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Active substances which can be employed in combination with the active substances according to the invention in mixed formulations or in the tank mix are, for example, known active substances as are described, for example, in Weed Research 26, 441–445 (1986) or "The Pesticide Manual", 11th edition, The British Crop Protection Council and the Royal Soc. of Chemistry, 1997 and literature cited therein. Known herbicides which are to be mentioned, and can be combined with the compounds of the formula (I), are, for example, the following active substances (note: the compounds are either designated by the common name according to the International Organization for Standardization (ISO) or using the chemical name, if appropriate together with a customary code number): acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluoro-2-phenyl-4H-3,1-benzoxazin-4-one; benazolin; benfluralin; benfuresate; bensulfuronmethyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butylester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethylester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentylester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; isocarbamid; isopropalin; isoproturon; isouron; isoxaben; isoxapyrifop; karbutilate; lactofen; lenacil; linuron; MCPA; MCPB; mecoprop; mefenacet; mefluidid; mesotrione; metamitron; metazachlor; metham; methabenzthiazuron; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; pirbuticarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy] propanoic acid and its methyl ester; suclotrione; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations, which are present in commercially available form, are diluted in the customary manner, for example using water in the case of wettable powders, emulsifiable concentrates, dispersions and water-dispersible granules. Preparations in the form of dusts, soil granules, granules for spreading and sprayable solutions are usually not diluted any further with other inert substances prior to use. The required application rate of the compounds of the formula (I) varies with the external conditions such as, inter alia, temperature, humidity and the nature of the herbicide used. It can vary within wide limits, for example between 0.001 and 1.0 kg/ha or more of active substance, but it is preferably between 0.005 and 750 g/ha.

The examples which follow illustrate the invention.

A. CHEMICAL EXAMPLES

The preparation of 5-hydroxypyrazoles was carried out in accordance with EP-A0 240 001.

1. Preparation of 4-(4-methylsulfonyl-3-(2-methoxyethylamino)-2-methylthiomethylbenzoyl)-5-hydroxy-1,3-dimethylpyrazole Step 1: Preparation of methyl 4-methylsulfonyl-3-fluoro-2-bromomethylbenzoate 30.75 g (0.12 mol) of methyl 2-methyl-3-fluoro-4-methylsulfonylbenzoate were introduced in 600 ml of $CCl_4$. 35.5 g (0.2 mol) of N-bromosuccinimide and 0.86 g (0.002 mol) of benzoyl peroxide were mixed. A third of the amount is added at RT. Then the batch is heated to reflux and "irradiated". Over the course of an hour the remaining NBS/benzoyl peroxide mixture is added in portions, followed by stirring under reflux for 2 h more. The batch is allowed to cool and is washed with a 10% strength sodium hydrogen sulfite solution, and dried over $MgSO_4$, and the organic phase is concentrated to completion.

Yield: 40.1 g (98% of theory)
$^1$H-NMR: δ[$CDCl_3$] 3.3 (s,3H), 4.05(s,3H), 5.0(s,2H), 7.9(d,1H) 8.0(d,1H)

Step 2: Preparation of methyl 4-methylsulfonyl-3-fluoro-2-methylthiomethylbenzoate 44.6 g (0.14 mol) of methyl 4-methylsulfonyl-3-fluoro-2-bromomethylbenzoate were dissolved in THF. 10.58 g (0.15 mol) of sodium thiomethoxide were added at RT and the mixture was then heated under reflux for 5 h. It was then poured onto ice-water and extracted with EE. The combined organic phases were dried over $MgSO_4$ and concentrated to completion.

Yield: 36.12 g (90% of theory)
$^1$H-NMR: δ[$CDCl_3$] 2.05 (s,3H), 3.25 (s,3H), 3.95 (s,3H), 4.2 (s,2H) 8.85 (d,1H), 8.95 (d,1H)

Step 3: 4-Methylsulfonyl-3-fluoro-2-methylthiomethylbenzoic acid 20 g (0.07 mol) of methyl 4-methylsulfonyl-3-fluoro-2-methylthiomethylbenzoate were dissolved in 400 ml of methanol, and 10.95 g (0.27 mol) of a 2N NaOH solution were added. The solution was stirred at RT for 4 h. The methanol was removed. The residue was taken up in water and acidified with 2N HCl. This was followed by extraction with $CH_2Cl_2$ and the organic phase was dried over $MgSO_4$ and concentrated to completion.

Yield: 18.3 g (96% of theory)
$^1$H-NMR: δ[$CDCl_3$] 2.1 (s,3H), 3.25 (s,3H), 4.2 s,2H), 7.95 (d,1H) 8.0 (d,1H)

Step 4: 4-Methylsulfonyl-3-(2-methoxyethylamino)-2-methylthiomethylbenzoic acid 2 g (7.2 mmol) of 4-methylsulfonyl-3-fluoro-2-methylthiomethylbenzoic acid were refluxed in 20 g (0.266 mol) of a 60% strength 2-methoxyethylamine solution in water for four days. The cold solution was acidified with concentrated HCl to a pH of 1 and extracted with EE. The organic solution was dried with $MgSO_4$ and concentrated to completion. This gives a brown oil.

Yield 2.31 g (96% of theory)
$^1$H-NMR: δ[$CDCl_3$] 2.1 (s,3H), 3.25 (s,3H), 3.4 (s,3H), 3.3 (t,2H), 3.6 (t,2H), 4.2 (s,2H), 7.6 (d,1H), 7.9 (d,1H)

Step 5: 1,3-Dimethyl-5-pyrazolyl(4-methylsulfonyl-3-(2-methoxyethylamino)-2-methylthiomethyl)benzoate (variant 1)

1.55 g (4.7 mmol) of 4-methylsulfonyl-3-(2-methoxyethylamino)-2-methylthiomethylbenzoic acid were introduced with 0.55 g (4.9 mmol) of 1,3-dimethyl-5-pyrazolone in 50 ml of $CH_2Cl_2$. Following the addition of a spatula tip of DMAP and 0.94 g (4.9 mmol) of N-(3-dimethylaminopropyl)-N-ethylcarbodiimide hydrochloride, the batch was stirred at RT for 4 h. After the end of reaction it was diluted with $CH_2Cl_2$ and washed with 1N HCl, water and $NaHCO_3$ solution. After drying with $MgSO_4$ the organic phase was concentrated to completion. The product was purified by means of column chromatography.

Yield: 0.6 g (28% of theory)
$^1$H-NMR: δ[$CDCl_3$] 2.0 (s,3H), 2.3 (s,3H), 3.15 (s,3H), 3.45 (s,3H), 3.5 (t, 2H), 3.6 (t,2H), 3.75 (s,3H), 4.2 (s,2H), 6.1(s, 1H), 7.6 (d,1H), 7.95 (d,1H)

Step 5: 1,3-Dimethyl-5-pyrazolyl(4-methylsulfonyl-3-(2-methoxyethylamino)-2-methylthiomethyl)benzoate (variant 2)

1.55 g (4.7 mmol) of 4-methylsulfonyl-3-(2-methoxyethylamino)-2-methylthiomethylbenzoic acid were dissolved in 90 ml of $CH_2Cl_2$. One drop of DMF and 0.63 g (5 mmol) of oxalyl chloride were added and the mixture was boiled under reflux for 4 h. Subsequently it was concentrated to completion, the residue was dissolved again in 90 ml of $CH_2Cl_2$, and 0.55 g (4.9 mmol) of 1,3-dimethyl-5-pyrazolone and 0.5 g (5 mmol) of $NEt_3$ were added. The batch was stirred at RT for 4 h. After the end of reaction it was diluted with $CH_2Cl_2$ and washed with 1N HCl, water and $NaHCO_3$ solution. After drying with $MgSO_4$ the organic phase was concentrated to completion. The product was purified by column chromatography.

Yield: 0.5 g (23% of theory)
$^1$H-NMR: [$CDCl_3$] 2.0 (s,3H), 2.3 (s,3H), 3.15 (s,3H), 3.45 (s,3H), 3.5 (t,2H), 3.6 (t,2H), 3.75 (s,3H), 4.2 (s,2H), 6.1(s, 1H), 7.6 (d,1H), 7.95 (d,1H)

Step 6: 4-(4-Methylsulfonyl-3-(2-methoxyethylamino)-2-methylthiomethylbenzoyl)-5-hydroxy-1,3-dimethylpyrazole 0.2 g (0.5 mmol) of 1,3-dimethyl-5-pyrazolyl (4-methylsulfonyl-3-(2-methoxyethylamino)-2-methylthiomethyl) benzoate were dissolved in 20 ml of acetonitrile. Following the addition of 2 drops of acetone cyanohydrin and 0.11 ml (0.8 mmol) of NEt$_3$, the mixture was stirred at RT for 2 h. Subsequently 0.01 g (0.2 mmol) of KCN was added and the mixture was stirred for a further 2 h. The solvent was then removed. The residue was taken up in water, acidified with 1N HCl to a pH of 1 and then extracted with CH$_2$Cl$_2$. After drying with MgSO$_4$ the organic phase was concentrated to completion. The product was purified by means of preparative HPLC.

Yield: 0.07 g (35% of theory)

$^1$H-NMR: δ[CDCl$_3$] 1.8 (s,3H), 2.05 (s,3H), 3.25 (s,3H), 3.4 (s,3H), 3.55 (t,2H), 3.6 (t,2H), 3.65 (s,3H), 3.85 (s,2H), 7.0(d, 1H), 7.95 (d,1H)

2. Preparation of 4-(4-methylsulfonyl-3-(2-methoxyethylamino)-1-(methylsulfonylmethyl)benzoyl-5-hydroxy-1-ethylpyrazole Step 1: 1-Ethyl-5-pyrazolyl(4-methylsulfonyl-3-(2-methoxyethylamino)-2-methylthiomethyl)benzoate 3.11 g (9.3 mmol) of 4-methylsulfonyl-3-(2-methoxyethylamino)-2-methylthiomethylbenzoic acid were introduced with 1.1 g (9.8 mmol) of 1-ethyl-5-pyrazolone in 100 ml of CH$_2$Cl$_2$. Following the addition of a spatula tip of DMAP and 1.88 g (9.8 mmol) of N-(3-dimethylaminopropyl)-N-ethylcarbodiimide hydrochloride the batch was stirred at RT for 4 h. After the end of reaction it was diluted with CH$_2$Cl$_2$ and washed with 1N HCl, water and NaHCO$_3$ solution. After drying with MgSO$_4$ the organic phase was concentrated to completion. The product was purified by means of column chromatography.

Yield: 2.31 g (58% of theory)

$^1$H-NMR: δ[CDCl$_3$] 1.4 (t,3H), 2.05 (s,3H), 3.25 (s,3H), 3.4 (s,3H), 3.45 (t,2H), 3.6 (t,2H), 4.1 (q,2H), 4.2 (s,2H), 6.25(s, 1H), 7.5 (s,1H), 7.6 (d,1H), 7.95 (d,1H)

Step 2: 1-Ethyl-5-pyrazolyl(4-methylsulfonyl-3-(2-methoxyethylamino)-2-(methylsulfonylmethyl)benzoate 1.5 g (3.5 mmol) of 1-ethyl-5-pyrazolyl (4-methylsulfonyl-3-(2-methoxyethylamino)-2-(methylthiomethyl)benzoate were cooled to 0° C. in 100 ml of CH$_2$Cl$_2$, and 2.16 g (8.8 mmol) of m-chloroperbenzoic acid were added in portions. The batch was allowed to warm to RT and was stirred at that temperature for 4 h. It was then diluted with 100 ml of CH$_2$Cl$_2$ and washed with NaHCO$_3$ solution, with Na$_2$S$_2$O$_3$ solution and then again with NaHCO$_3$ solution. The organic phase was dried with MgSO$_4$ and concentrated to completion.

Yield: 1.33 g (82% of theory)

$^1$H-NMR: δ[CDCl$_3$] 1.4 (t,3H), 2.9 (s,3H), 3.35 (s,3H), 3.45 (t,2H), 3.5 (s,3H), 3.6 (t,2H), 4.1 (q,2H), 6.2 (s, 1H), 7.5 (s,1H), 7.95 (d,1H), 8.2 (d,1H)

Step 3: 4-(4-Methylsulfonyl-3-(2-methoxyethylamino)-1-(methylsulfonylmethyl)benzoyl-5-hydroxy-1-ethylpyrazole 0.3 g (0.7 mmol) of 1-ethyl-5-pyrazolyl (4-methylsulfonyl-3-(2-methoxyethylamino)-2-(methylsulfonylmethyl) benzoate were dissolved in 20 ml of acetonitrile. Following the addition of 2 drops of acetone cyanhydrin and 0.12 ml (1.1 mmol) of NEt$_3$, the batch was stirred at RT for 2 h. Then 0.02 g (0.3 mmol) of KCN was added and stirring was continued for 2 h. The solvent was then removed. The residue was taken up in water, acidified with 1N HCl to a pH of 1 and then extracted with CH$_2$Cl$_2$. After drying with MgSO$_4$ the organic phase was concentrated to completion. The product was purified by means of preparative HPLC.

Yield: 0.1 g (33% of theory)

$^1$H-NMR: δ[CDCl$_3$] 1.4 (t,3H), 2.9 (s,3H), 3.35 (s,3H), 3.4 (s,3H), 3.4 (t,2H), 3.6 (t,2H), 4.1 (q,2H), 5.0 (s,2H), 7.45 (s,1H), 7.5 (d,1H), 8.15 (d,1H)

The examples listed in the table below were prepared in analogy to methods specified above or are obtainable in analogy to methods specified above.

The abbreviations used here have the following definitions:

| | | |
|---|---|---|
| Bn = benzyl | Bu = n-butyl | Bz = benzoyl |
| c-Pr = cyclopropyl | Et = ethyl | Me = methyl |
| Ph = phenyl | Pr = n-propyl | |
| EE = ethyl acetate | m.p. = melting point | RT = room temperature |

TABLE 1

| No. | Structure | Physical data* |
|---|---|---|
| 1 | [structure: pyrazole with H$_3$C, N-N-CH$_3$, OH, connected via C=O to benzene ring with CH$_2$SCH$_3$, NH$_2$, Br substituents] | $^1$H-NMR: δ[CDCl$_3$] 1.78 (s, 3H), 2.02 (s, 3H), 3.6 (s, 3H), 3.75 (s, 2H), 4.85 (s, 2H), 6.58(d, 1H), 7.45 (d, 1H) |
| 2 | [structure: pyrazole with cyclopropyl, N-N-CH$_3$, OH, connected via C=O to benzene ring with CH$_2$SO$_2$CH$_3$, NH$_2$, Br substituents] | $^1$H-NMR: δ[CDCl$_3$] 0.65 (m, 2H), 0.85 (m, 2H), 1.05 (mt, 1H), 2.99 (s, 3H), 4.59 (s, 2H), 5.15 (s, 2H), 6.85(d, 1H), 7.55 (d, 1H) |

TABLE 1-continued

| No. | Structure | Physical data* |
|---|---|---|
| 3 | 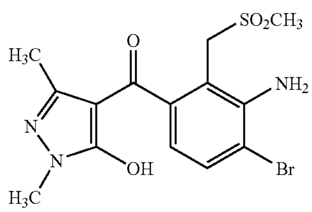 | ¹H-NMR: δ[CDCl₃] 1.8 (s, 3H), 2.99 (s, 3H), 3.61 (s, 3H), 4.55 (s, 2H), 5.15 (s, 2H), 6.7(d,1H), 7.58 (d, 1H) |
| 4 | 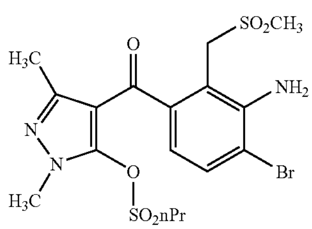 | ¹H-NMR: δ[CDCl₃] 1.05 (t, 3H), 1.8 (m, 2H), 2.2 (s, 3H), 3.02 (t, 2H), 3.05 (s, 3H), 3.79 (s, 3H), 4.6 (s, 2H), 5.2 (s, 2H), 6.75 (d, 1H), 7.55 (d, 1H) |
| 5 | 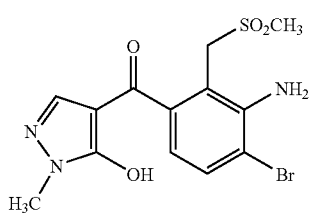 | |
| 6 | 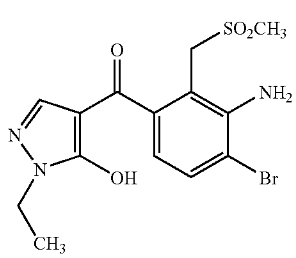 | ¹H-NMR: δ[CDCl₃] 1.45 (t, 3H), 3.0 (s, 3H), 4.05 (q, 2H), 4.7 (s, 2H), 6.98 (d, 2H), 7.62 (d, 1H) |
| 7 | 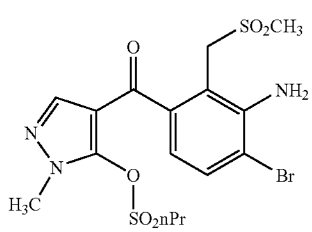 | |
| 8 | 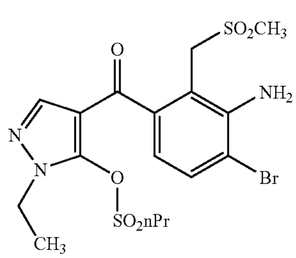 | |

TABLE 1-continued

| No. | Structure | Physical data* |
|---|---|---|
| 9 | 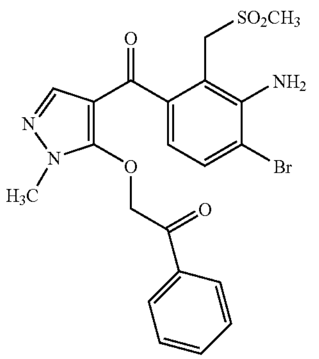 | |
| 10 | 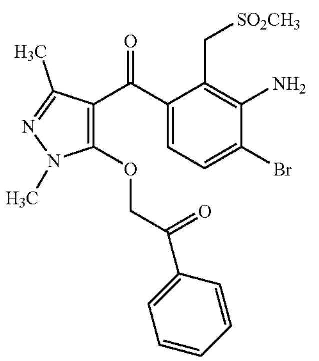 | |
| 11 | 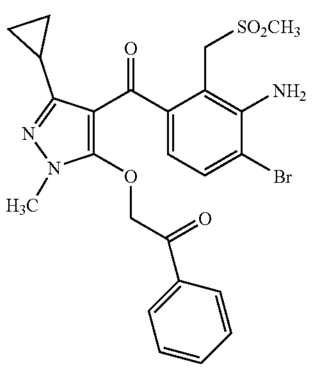 | |
| 12 | 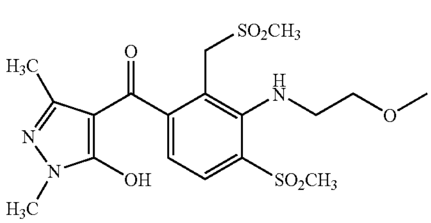 | $^1$H-NMR: δ[CDCl$_3$] 1.85 (s, 3H), 2.92 (s, 3H), 3.39 (s, 3H), 3.42 (s, 3H), 3.42 (7, 2H), 3.59 (t, 2H), 3.62 (s, 3H), 4.85 (s, 2H), 7.3 (d, 1H), 8.15 (d, 1H) |
| 13 | 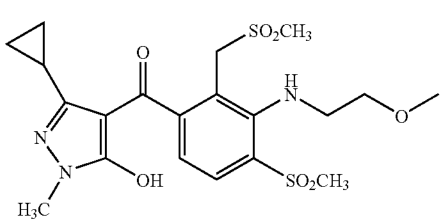 | $^1$H-NMR: δ[CDCl$_3$] 0.6 (m, 2H), 0.85 (m, 2H), 1.15 (mt, 1H), 2.9 (s, 3H), 3.4 (s, 3H), 3.42 (t, 2H), 3.42 (s, 3H), 3.58 (t, 2H), 3.6 (s, 3H), 4.9 (s, 2H), 5.2 (s, 1H), 7.45 (d, 1H), 8.15 (d, 1H) |

TABLE 1-continued

| No. | Structure | Physical data* |
|---|---|---|
| 14 | 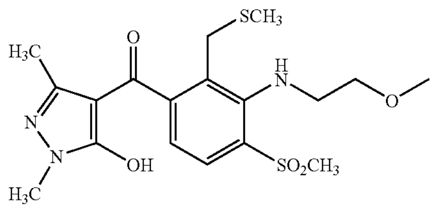 | ¹H-NMR: δ[CDCl₃] 1.8 (s, 3H), 2.05 (s, 3H), 3.25 (s, 3H), 3.4 (s, 3H), 3.55 (t, 2H), 3.6 (t, 2H), 3.65 (s, 3H), 3.85 (s, 2H), 7.0 (d, 1H), 7.95 (d, 1H) |
| 15 | 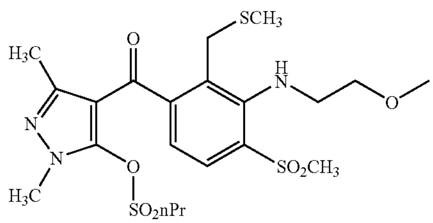 | |
| 16 | 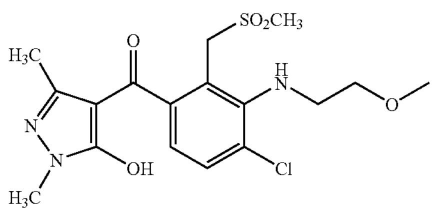 | |
| 17 | 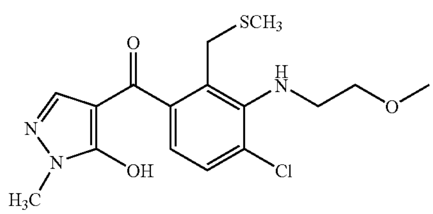 | |
| 18 | 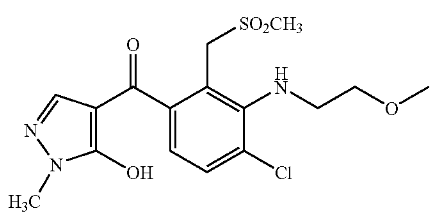 | |
| 19 | 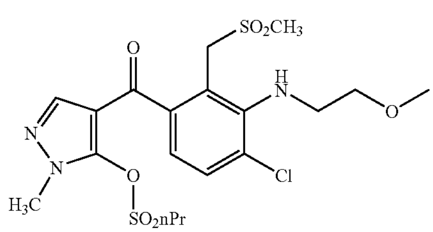 | |
| 20 | 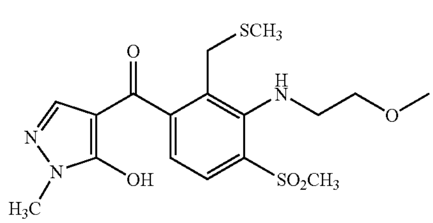 | ¹H-NMR: δ[CDCl₃] 2.18 (s, 3H), 3.26 (s, 3H), 3.4 (s, 3H), 3.5 (t, 2H), 3.6 (t, 2H), 3.72 (s, 3H), 4.0 (s, 2H), 7.2 (d, 1H), 7.4 (s, 1H), 7.96 (d, 1H) |

TABLE 1-continued

| No. | Structure | Physical data* |
|---|---|---|
| 21 | 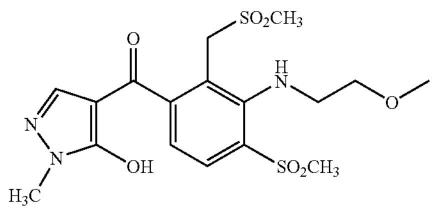 | |
| 22 | 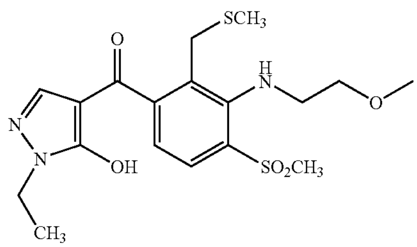 | |
| 23 | 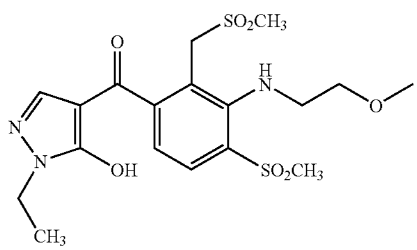 | $^1$H-NMR: δ[CDCl$_3$] 1.4 (t, 3H), 2.9 (s, 3H), 3.35 (s, 3H), 3.4 (s, 3H), 3.4 (t, 2H), 3.6 (t, 2H), 4.1 (q, 2H), 5.0 (s, 2H), 7.45 (s, 1H), 7.5 (d, 1H), 8.15 (d, 1H) |
| 24 | 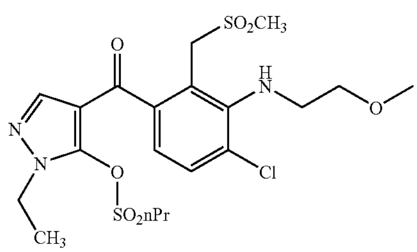 | |
| 25 | 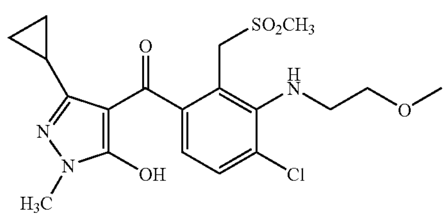 | |
| 26 | 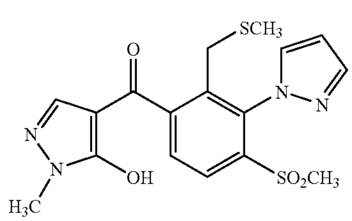 | |

TABLE 1-continued

| No. | Structure | Physical data* |
|-----|-----------|----------------|
| 27  | 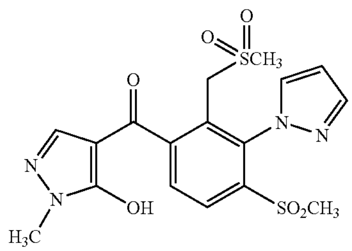          |                |
| 28  | 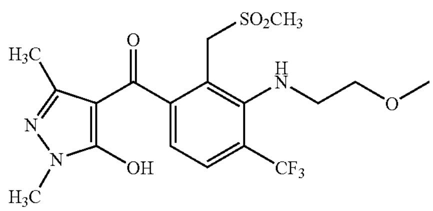          |                |
| 29  | 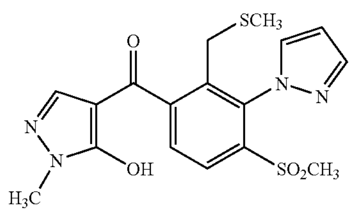          |                |
| 30  | 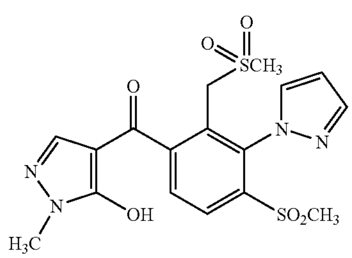          |                |
| 31  | 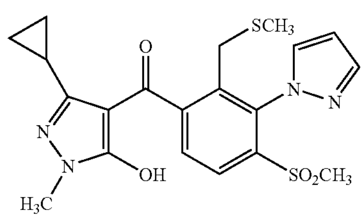          |                |
| 32  | 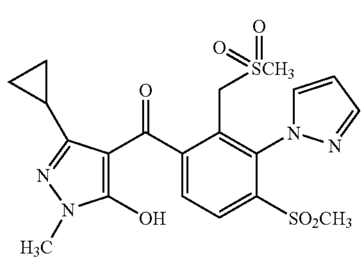          |                |

TABLE 1-continued

| No. | Structure | Physical data* |
|---|---|---|
| 33 | 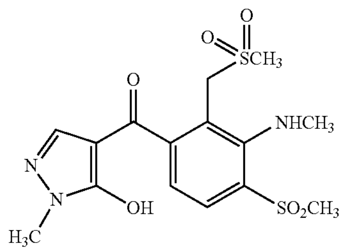 | |
| 34 | 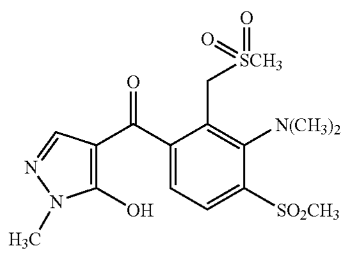 | |
| 35 | 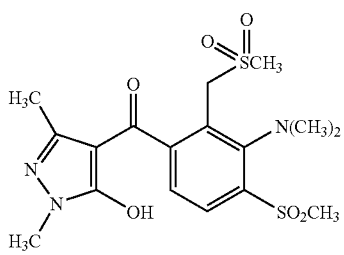 | |
| 36 | 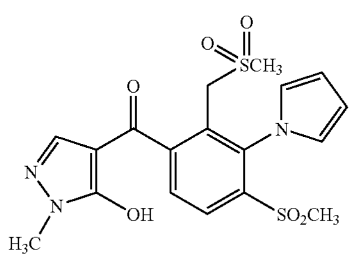 | |
| 37 | 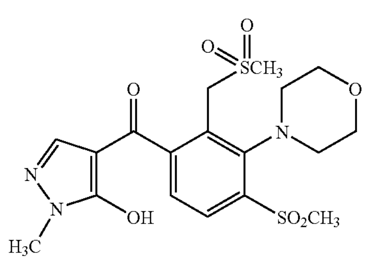 | |
| 38 | 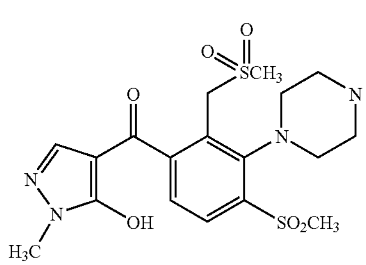 | |

TABLE 1-continued

| No. | Structure | Physical data* |
|---|---|---|
| 39 | 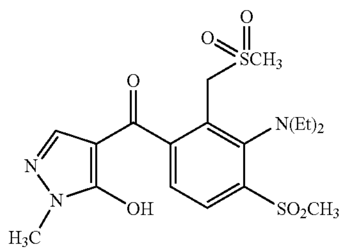 | |
| 40 | 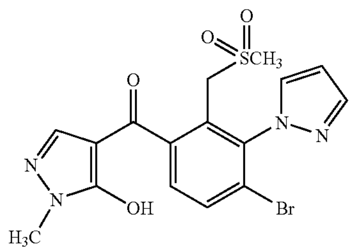 | |
| 41 | 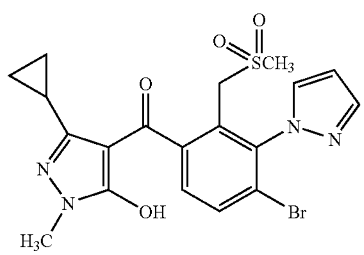 | |
| 42 | 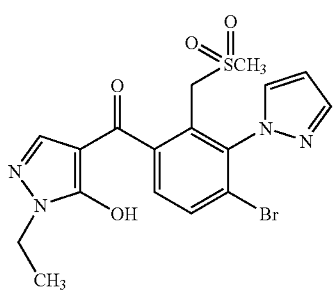 | |
| 43 | 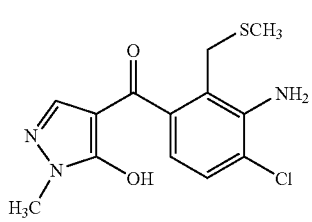 | $^1$H-NMR: δ[CDCl$_3$] 2.0 (s, 3H), 3.7 (s, 3H), 3.9 (s, 2H), 4.4 (s, 2H), 6.9 (d, 1H), 7.3 (d, 1H), 7.4 (s, 1H) |
| 44 | 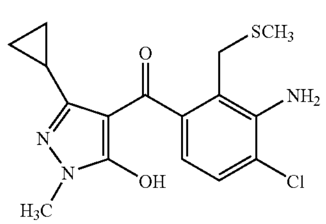 | $^1$H-NMR: δ[CDCl$_3$] 0.6 (m, 2H), 0.8 (m, 2H), 1.1 (m, 1H), 2.0 (s, 3H), 3.6 (s, 3H), 3.8 (s, 2H), 4.9 (s, 2H), 6.8 (d, 1H), 7.3 (d, 1H) |

TABLE 1-continued

| No. | Structure | Physical data* |
|---|---|---|
| 45 | (structure: pyrazole with N-ethyl, OH, C(=O) linked to phenyl bearing CH2SCH3, NH2, Cl) | ¹H-NMR: δ[CDCl₃] 1.5 (t, 3H), 2.0 (s, 3H), 3.9 (s, 2H), 4.1 (q, 2H), 4.8 (s, 2H), 6.9 (d, 1H), 7.3 (d, 1H), 7.4 (s, 1H) |
| 46 | (structure: 3-methyl-1-methyl pyrazole with OH, C(=O) linked to phenyl bearing CH2SCH3, NH2, Cl) | ¹H-NMR: δ[CDCl₃] 1.8 (s, 3H), 2.0 (s, 3H), 3.6 (s, 3H), 3.7 (s, 2H), 4.8 (s, 2H), 6.6 (d, 1H), 7.3 (d, 1H) |

B. Formulation Examples

1. Dust

A dust is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing 25 parts by weight of a compound of the formula (I), 64 parts by weight of kaolin-containing quartz as inert substance, 10 parts by weight of potassium ligninsulfonate and 1 part by weight of sodium oleoylmethyltauride as wetter and dispersant, and grinding the mixture in a pinned-disk mill.

3. Dispersion Concentrate

A dispersion concentrate which is readily dispersible in water is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

4. Emulsifiable Concentrate

An emulsifiable concentrate is obtained from 15 parts by weight of a compound of the formula (I), 75 parts by weight of cyclohexanone as solvent and 10 parts by weight of oxethylated nonylphenol as emulsifier.

5. Water-dispersible Granules

Water-dispersible granules are obtained by mixing
75 parts by weight of a compound of the formula (I),
10" calcium ligninsulfonate,
5" sodium lauryl sulfate,
3" polyvinyl alcohol and
7" kaolin, grinding the mixture in a pinned-disk mill and granulating the powder in a fluidized bed by spraying on water as granulation liquid.

Water-dispersible granules are also obtained by homogenizing and precomminuting, in a colloid mill,
25 parts by weight of a compound of the formula (I),
5" sodium 2,2'-dinaphthylmethane-6,6'-disulfonate,
2" sodium oleoylmethyltauride,
1" polyvinyl alcohol,
17" calcium carbonate and
50" water, subsequently grinding the mixture in a bead mill, and atomizing and drying the resulting suspension in a spray tower by means of a single-fluid nozzle.

C. Biological Examples

1. Pre-Emergence Weed Action

Seeds of mono- and dicotyledonous broadleaf weed plants are placed in sandy loam in cardboard pots and covered with soil. The compounds according to the invention, formulated as wettable powders or emulsifiable concentrations, are then applied, in the form of an aqueous suspension or emulsion, at various dosages, onto the surface of the covering earth, at an application rate of 600 to 800 l of water per ha (converted). Following treatment, the pots are placed in the greenhouse and maintained under good growth conditions for the broadleaf weeds. The visual scoring of the plant damage or emergence damage is made when the test plants have emerged, after an experimental period of 3 to 4 weeks, in comparison to untreated controls. In this experiment the compounds of the invention have outstanding activity against a broad spectrum of economically important monocotyledonous and dicotyledonous weed plants. Thus, for example, the compounds of Nos 2 and 3 according to the invention, at a dosage of 320 g/ha, exhibit an action of at least 90% against the weed plants *Stellaria media, Amaranthus retroflexus, Chenopodium album, Veronica persica* and *Abutilon theophrasti*.

2. Post-emergence Herbicidal Action Against Weed Plants

Seeds of mono- and dicotyledonous weed plants are placed in sandy loam in cardboard pots, covered with soil and grown in the greenhouse under good growth conditions. Two to three weeks after sowing, the test plants are treated at the three-leaf stage. The compounds according to the invention, formulated as wettable powders or as emulsifiable concentrates, are sprayed at various dosages onto the surface of the green plant parts at an application rate of 600 to 800 l of water per ha (converted). After the test plants have been left to stand in the greenhouse for 3 to 4 weeks under optimal growth conditions, the effect of the compounds is scored. In this test the compounds according to the invention exhibit outstanding activity against a broad spectrum of economically important monocotyledonous and dicotyledonous weed plants. Thus, for example, compound No. 4 according to the invention, at a dosage of 320 g/ha, exhibits an activity of at least 90% against the weed plants *Setaria viridis, Echinochloa crus-galli, Sinapis arvensis, Stellaria media, Amaranthus retroflexus, Chenopodium album* and *Fallopia convolvulus.*

3. Crop Plant Tolerance

In further greenhouse experiments, seeds of barley and of monocotyledonous and dicotyledonous weed plants are placed in sandy loam, covered with soil and placed in the greenhouse until the plants have developed two to three true leaves. Then they are treated with the compounds of the formula (I) according to the invention, as described above in section 2. Four to five weeks after the application and after having been left to stand in the greenhouse, visual scoring reveals that the compounds according to the invention are outstandingly well tolerated by important crop plants, in particular wheat, maize and rice. Thus, for example, compound No. 6 according to the invention, at a dosage of 100 g/ha, exhibits an action of at least 95% against the weed plants *Echinochloa crus-galli, Sagittaria pygmaea, Cyperus serotinus* and *Scirpus juncoides,* and at the same time causes no damage to the crop plant rice.

What is claimed is:

1. A compound of the formula (I) or salt thereof

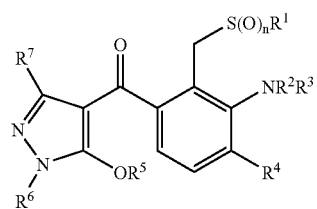

(I)

in which $R^1$ is $C_1$–$C_6$alkyl;

$R^2$ and $R^3$ independently of one another are hydrogen, $C_3$–$C_6$cycloalkyl, $C_2$–$C_6$alkenyl, $C_2$–$C_6$alkynyl or $C_1$–$C_6$alkyl substituted s times by radicals from the group consisting of halogen, $C_1$–$C_4$alkoxy and $C_1$–$C_4$alkylthio, or $NR^2R^3$ forms a 5- or 6-membered heterocyclic radical from the group consisting of 1-pyrrolyl, 1-pyrrolidinyl, 1-piperidinyl, 1-pyrazolyl, 1,2,3-triazol-1-yl, 1,2,4-triazol-1-yl, 1-tetrazolyl, 1-pyrazolidinyl, 1-imidazolyl, 2-isoxazoldinyl, 3-oxazolidinyl, 1,2,3-oxadiazolidin-2-yl, 1,2,3-oxadiazolidin-3-yl, 1,2,4-oxadiazolidin-2-yl, 1,2,3-oxadiazolidin-4-yl, 1,3,4-oxadiazolidin-3-yl, 1,3,4-oxadiazolidin-4-yl, 3-thiazolidinyl, 2,3-thiadiazolidin-2-yl, 1,2,3-thiadiazolidin-3-yl, 1,2,4-thiadiazolidin-2-yl, 1,2,3-thiadiazolidin-4-yl, 1,3,4-thiadiazolidin-3-yl, 1,3,4-thiadiazolidin-4-yl, 1-morpholinyl, 2,3-dihydropyrrol-1-yl, 2,5-dihydropyrrol-1-yl, 2,3-dihydroisoxazol-2-yl, 2,5-dihydroisothiazol-1-yl, 1,2-dihydropyridin-1-yl, 1,4-dihydropyridin-1-yl, 3,4,5,6-tetrahydropyridin-1-yl, 1-piperazinyl and 1-tetrahydropyrimidinyl, the aforementioned heterocyclic radicals being substituted s times by substituents from the group consisting of halogen, cyano, $C_1$–$C_4$alkoxy, trifluoromethyl, trifluoroethyl, fluoro-$C_1$–$C_3$alkyl, fluoro-$C_1$–$C_3$alkoxy, cyano-$C_1$–$C_4$alkyl, $C_3$–$C_6$cycloalkyl, $C_3$–$C_6$cycloalkyl-$C_1$–$C_4$-alkyl, $C_1$–$C_3$alkoxymethyl;

$R^4$ is hydrogen, halogen, $C_1$–$C_4$alkyl, halo-$C_1$–$C_4$alkyl, $C_1$–$C_4$alkoxy, $C_1$–$C_4$alkylthio, $C_1$–$C_4$alkylsulfinyl or $C_1$–$C_4$alkylsulfonyl;

$R^5$ is hydrogen, $C_1$–$C_6$alkylcarbonylmethyl, phenylsulfonyl, $C_1$–$C_4$ alkylsulfonyl substituted s times by halogen, phenylsulfonyl substituted once by methyl or halogen, benzyl substituted s times by halogen, nitro or methoxy, or benzoylmethyl substituted s times by halogen, nitro, methyl or methoxy;

$R^6$ is $C_1$–$C_4$alkyl;

$R^7$ is hydrogen, $(C_1$–$C_4)$alkyl or $C_3$–$C_6$cycloalkyl;

n is 0, 1 or 2;

s is 0, 1, 2 or 3;

t is 1, 2 or 3.

2. A compound as claimed in claim 1, wherein $R^1$ is methyl;

$R^2$ and $R^3$ independently of one another are hydrogen, cyclopropyl, $C_1$–$C_6$alkyl, $C_2$–$C_6$alkenyl, $C_2$–$C_6$alkynyl or $C_1$–$C_6$alkyl substituted by a $C_1$–$C_4$alkoxy radical, or $NR^2R^3$ forms a 5- or 6-membered heterocyclic radical from the group consisting of 1-pyrrolyl, 1-pyrrolidinyl, 1-piperidinyl, 1-pyrazolyl, 1,2,3-triazol-1-yl, 1,2,4-triazol-1-yl, 1-tetrazolyl, 1-pyrazolidinyl, 1-imidazolyl, 2-isoxazoldinyl, 3-oxazolidinyl, 1,2,3-oxadiazolidin-2-yl, 1,2,3-oxadiazolidin-3-yl, 1,2,4-oxadiazolidin-2-yl, 1,2,3-oxadiazolidin-4-yl, 1,3,4-oxadiazolidin-3-yl, 1,3,4-oxadiazolidin-4-yl, 3-thiazolidinyl, 2,3-thiadiazolidin-2-yl, 1,2,3-thiadiazolidin-3-yl, 1,2,4-thiadiazolidin-2-yl, 1,2,3-thiadiazolidin-4-yl, 1,3,4-thiadiazolidin-3-yl, 1,3,4-thiadiazolidin-4-yl, 1-morpholinyl, 2,3-dihydropyrrol-1-yl, 2,5-dihydropyrrol-1-yl, 2,3-dihydroisoxazol-2-yl, 2,5-dihydroisothiazol-1-yl, 1,2-dihydropyridin-1-yl, 1,4-dihydropyridin-1-yl, 3,4,5,6-tetrahydropyridin-1-yl, 1-piperazinyl and 1-tetrahydropyrimidinyl, the abovementioned heterocyclic radicals being substituted s times by substituents from the group consisting of halogen, methoxy and trifluoromethyl, and n is 0 or 2.

3. A compound as claimed in claim 1, wherein $R^4$ is bromine, chlorine, fluorine, trifluoromethyl, methylsulfonyl or ethylsulfonyl, and $R^5$ is hydrogen, n-propylsulfonyl or benzoylmethyl.

4. A compound as claimed in 1, wherein $R^6$ is methyl or ethyl, and $R^7$ is hydrogen, methyl or cyclopropyl.

5. A compound as claimed in claim 1, wherein $R^2$ and $R^3$ independently of one another are hydrogen, methyl, ethyl, cyclopropyl or methoxyethyl, or $NR^2R^3$ forms a radical from the group consisting of 1-pyrrolyl, 1-pyrazolyl, 1-morpholinyl and 1-piperazinyl.

6. A herbicidal composition comprising a herbicidally effective amount of at least one compound of the formula (I) as claimed in claim 1.

7. A herbicidal composition as claimed in claim 6 in a mixture with formulating auxiliaries.

8. A method of controlling unwanted plants, which comprises applying an effective amount of at least one compound of the formula (I) as claimed in claim 1 to the plants or to the site of the unwanted plant growth.

9. A compound as claimed in claim 2, wherein
$R^4$ is bromine, chlorine, fluorine, trifluoromethyl, methylsulfonyl or ethylsulfonyl, and
$R^5$ is hydrogen, n-propylsulfonyl or benzoylmethyl.

10. A method of controlling unwanted plants, which comprises applying an effective amount of a herbicidal composition as claimed in claim 6 to the plants or to the site of the unwanted plant growth.

11. A method of controlling unwanted plants, which comprises applying an effective amount of a herbicidal composition as claimed in claim 7 to the plants or to the site of the unwanted plant growth.

12. The method of claim 8, wherein the unwanted plants are in crops of useful plants.

13. The method of claim 12, wherein the useful plants are transgenic.

14. The method of claim 10, wherein the unwanted plants are in crops of useful plants.

15. The method of claim 14, wherein the useful plants are transgenic.

16. The method of claim 11, wherein the unwanted plants are in crops of useful plants.

17. The method of claim 16, wherein the useful plants are transgenic.

* * * * *